United States Patent
Koga et al.

(10) Patent No.: US 8,772,540 B2
(45) Date of Patent: Jul. 8, 2014

(54) THERMAL RESPONSIVE MOLECULE

(75) Inventors: Noboru Koga, Fukuoka (JP); Satoru Karasawa, Fukuoka (JP); Hiroyuki Hayashi, Fukuoka (JP)

(73) Assignee: Kyushu University, National University Corporation, Fukuoka-shi (JP)

( * ) Notice: Subject to any disclaimer, the term of this patent is extended or adjusted under 35 U.S.C. 154(b) by 751 days.

(21) Appl. No.: 12/950,098

(22) Filed: Nov. 19, 2010

(65) Prior Publication Data

US 2011/0124916 A1    May 26, 2011

Related U.S. Application Data

(60) Provisional application No. 61/262,633, filed on Nov. 19, 2009.

(51) Int. Cl.
*C07C 275/00* (2006.01)

(52) U.S. Cl.
USPC ............................................. 564/50

(58) Field of Classification Search
USPC ............................................. 564/50
See application file for complete search history.

(56) References Cited

U.S. PATENT DOCUMENTS 4,118,418 A * 10/1978 Conrow et al. ............... 562/439

OTHER PUBLICATIONS

Judith J. van Gorp, Jef A. J. M. Vekemans, and E. W. Meijer., J. Amer. Chem. Soc., 2002, 124, 14759-14769.*
Matthew C. Davis, Synthetic Communicationsw, 37: 3519-3528, 2007.*

* cited by examiner

*Primary Examiner* — Fereydoun G Sajjadi
*Assistant Examiner* — Kofi Adzamli
(74) *Attorney, Agent, or Firm* — Edwards Wildman Palmer LLP

(57) ABSTRACT

Provided is a thermal responsive molecule favorable as a thermal responsive low-molecular hydrogelling agent or the like that gels in response to heat. The thermal responsive molecule is characterized in that an amphiphilic side chain obtained by bonding a hydrophilic side chain such as triethylene glycol and a hydrophobic group such as an octyl group is introduced into a $C_3$-symmetric disc-shaped molecular skeleton such as 1,3,5-benzenetriyltriurea. For example, the thermal responsive molecule is 1,1',1"-(benzene-1,3,5-triyl) tris{3-(2,5,8,11-tetraoxaheptadecan-17-yl)urea} or the like.

4 Claims, 4 Drawing Sheets

25°C　　　　　　40°C　　　　　40°C–50°C　　　　　50°C<
Semitransparent Gel　Clouded Gel　Contraction　Phase Separation

THERMAL RESPONSIVE MOLECULE

CROSS-REFERENCE TO RELATED APPLICATIONS

The present application claims priority to U.S. provisional application 61/262,633, filed Nov. 19, 2009, the entire description of which is herein incorporated by reference especially as disclosure.

FIELD OF THE INVENTION

The present invention relates to a thermal responsive molecule suitable as a thermal responsive low-molecular hydrogelling agent or the like that gels when heated.

BACKGROUND ART

Recently, a stimulus-responsive hydrogel that gels in response to external stimulus such as heat, pH, light or the like has been expected to be applicable to a broad field as a substrate for tissue regeneration materials and slow-release preparations and as an absorbent for harmful substances, and its studies are being much promoted. In particular, PNIPAM (poly(N-isopropyl acrylamide)) or the like known as a temperature-responsive polymer is known to have LCST (lower critical solution temperature) at or above which the solubility in water of the polymer dramatically lowers, and the presence of a thermal responsive hydrogel to form a hydrogel at or above LCST based on this phenomenon is reported. However, in expecting biological application, the polymer such as PNIPAM has a drawback in that its biodegradability is poor. As opposed to this, a low-molecular hydrogel is expected to reduce the load to living bodies since it is a low-molecular aggregate integrated through the noncovalent bondings such as hydrophobic interaction or hydrogen bonding. Accordingly, the necessity for a temperature-responsive low-molecular hydrogelling agent would increase more and more. However, as an example of its report, there may be found only Non-Patent Reference 1 by Hamachi et al mentioned below.

PRIOR ART REFERENCE

Non-Patent Reference

Non-Patent Reference 1: Hamachi et al., Journal of the American Chemical Society, Vol. 131, 5580, 2009

SUMMARY OF THE INVENTION

Problem to be Solved by Invention

Accordingly, an object of the invention is to provide a thermal responsive molecule suitable as a thermal responsive low-molecular hydrogelling agent or the like that gels in response to heat.

Means for Solving Problem

As a result of assiduous studies for solving the above-mentioned problems, the present inventors produced 1,1',1''-(benzene-1,3,5-triyl)-tris{3-(2,5,8,11-tetraoxaheptadecan-17-yl)urea} (hereinafter abbreviated as "$Eg_3C_8U$"), in which an amphiphilic side chain obtained by bonding a hydrophilic triethylene glycol chain and a hydrophobic octyl group is introduced into a $C_3$-symmetric disc-shaped molecule, 1,3,5-benzenetriyltriurea skeleton, and it has been clarified that the $Eg_3C_8U$ forms a thermal responsive hydrogel which dissolves at a low temperature and gels when heated, and that its lowermost gelling concentration is 0.05 wt. % and the compound gels in an extremely dilute solution. A thermal responsive hydrogel heretofore known in the prior art generally gels when cooled, but contrary to this, it has been clarified that the thermal responsive molecule of the invention gels when heated, and has the property of reverse gel.

The invention has been made on the basis of these findings, and the thermal responsive molecule of the invention is, as stated in claim 1, represented by the following general formula (1), in which an amphiphilic side chain obtained by bonding a hydrophilic side chain and a hydrophobic group is introduced into a $C_3$-symmetric disc-shaped molecular skeleton:

$$Eg_nC_mU \quad (1)$$

wherein Eg represents ethylene glycol; n indicates an integer of from 3 to 10; C represents an aliphatic hydrocarbon group; m indicates an integer of from 2 to 15; and U represents an urea skeleton.

The thermal responsive molecule stated in claim 2 is the thermal responsive molecule according to claim 1, wherein U is 1,3,5-benzenetriyltriurea or 1,3,5-benzenetriyltriamide.

The thermal responsive molecule stated in claim 3 is the thermal responsive molecule according to claim 1, wherein n is 3, m is 8, and U is 1,3,5-benzenetriyltriurea.

The thermal responsive molecule stated in claim 4 is the thermal responsive molecule according to claim 3, wherein the thermal responsive molecule is a low-molecular hydrogelling agent.

The thermal responsive molecule stated in claim 5 is the thermal responsive molecule according to claim 1, wherein the thermal responsive molecule is $Eg_6TC_6U$.

Effect of Invention

The thermal responsive molecule of the invention is represented by the above-mentioned general formula (I), in which an amphiphilic side chain obtained by bonding a hydrophilic side chain and a hydrophobic group is introduced into a $C_3$-symmetric disc-shaped molecular skeleton, and is a low-molecular aggregate integrated through noncovalent bondings such as hydrophobic interaction or hydrogen bonding, therefore bringing about a temperature-responsive low-molecular hydrogelling agent or the like whose load to living bodies is reduced.

Figure 1:
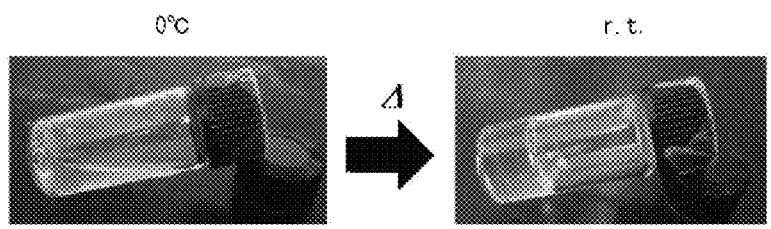
FIG. 1 includes photographic pictures showing the gellation of a thermal responsive molecule (hydrogelling agent) of the invention.

Embodiments of the invention are described concretely hereinunder with reference to Examples; however, the invention is not limited to these Examples.

The thermal responsive molecule of the invention is represented by the above-mentioned general formula (I), in which an amphiphilic side chain obtained by bonding a hydrophilic side chain and a hydrophobic group is introduced into a $C_3$-symmetric disc-shaped molecular skeleton.

U that constitutes the $C_3$-symmetric disc-shaped molecular skeleton includes 1,3,5-benzenetriyltriurea, 1,3,5-benzenetriyltriamide, etc. From the viewpoint of the intermolecular hydrogen bonding, preferred is 1,3,5-benzenetriyltriurea.

In $Eg_n$ that constitutes the hydrophilic side chain, n is defined to be from 3 to 10 from the viewpoint of the suitable solubility of the molecule in water; but preferred is triethylene glycol with n=3, or tetraethylene glycol with n=4.

In the hydrophobic group $C_m$ that constitutes the amphiphilic side chain, m is defined to be from 2 to 15 from the viewpoint of the molecular aggregation in water; but preferred is an octyl group with m=8 from the viewpoint of the suitable solubility of the molecule in water.

The amphiphilic side chain may be modified in any manner not detracting from the thermal responsiveness of the molecule.

The thermal responsive molecule of the invention can be produced according to the following scheme:

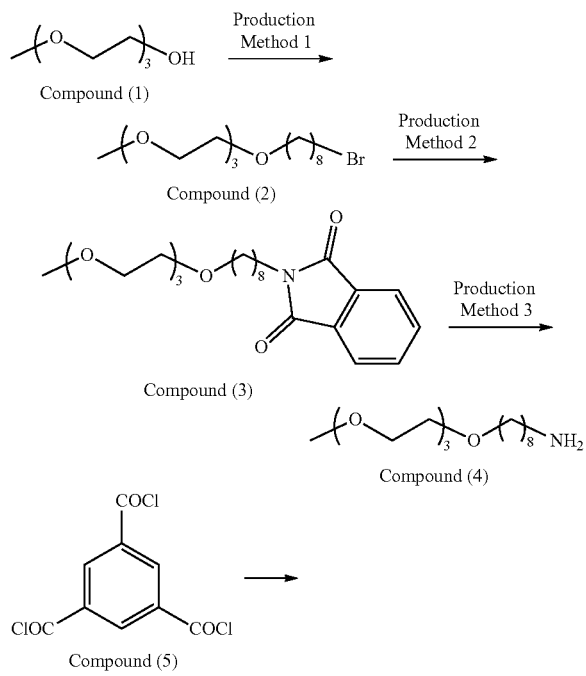

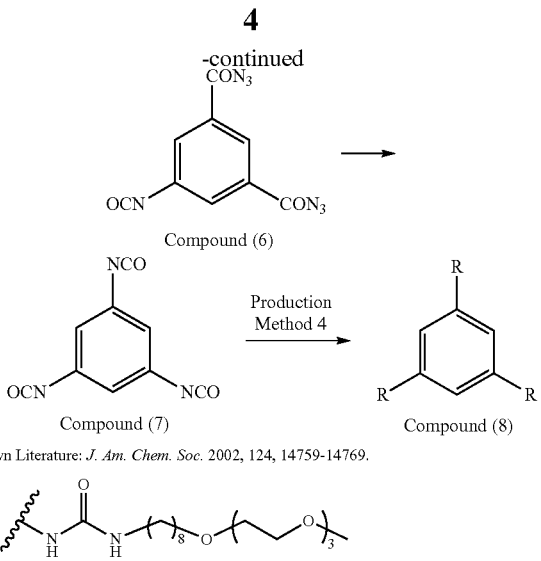

Known Literature: *J. Am. Chem. Soc.* 2002, 124, 14759-14769.

Embodiments of the invention are described more concretely hereinunder with reference to Examples; however, the invention is not limited to these Examples.

A thermal responsive molecule (hydrogel) of the invention was produced according to the above-mentioned production process.

<Production of Compound (2) According to Production Method 1>

731 mg (18.3 mmol) of 60% sodium hydride was washed twice with hexane, then dissolved in 10 ml of N,N-dimethylformamide and stirred on an ice bath. A solution of 1.5 g (9.1 mmol) of triethylene glycol monomethyl ether (compound (1)) dissolved in 5 ml of N,N-dimethylformamide was dropwise added to the above solution, taking 5 minutes. 12.4 g (45.7 mmol) of 1,8-dibromooctane was dissolved in 10 ml of N,N-dimethylformamide in a different chamber in a nitrogen atmosphere, and stirred on an ice bath. The first prepared solution was dropwise added to this solution, taking 20 minutes. Subsequently, this was stirred for 3 and a half hours with gradually heating up to room temperature. Water was added thereto to stop the reaction, and then this was extracted with hexane. This was dried with magnesium sulfate, and the solvent was evaporated away. This was purified through silica gel column chromatography (hexane/ethyl acetate) to give 2.21 g of a colorless transparent liquid of 17-bromo-2,5,8,11-tetraoxaheptadecane, $Eg_3C_6Br$ (compound (2)).

IR (NaCl, $cm^{-1}$) 2929, 2858, 1457, 1351, 1289, 1247, 1200, 1112, 1031, 942, 851, 724, 644

$^1$H NMR ($CDCl_3$, 270 MHz) δ 3.40-3.68 (m, 16H), 3.39 (s, 3H), 1.85 (quint, J=6.7 Hz, 2H), 1.24-1.58 (m, 10H)

FABMS (m-nitrobenzyl alcohol) m/z 355.3 [M+1], 377.2 [M+Na]

<Production of Compound (3) According to Production Method 2>

1.8 g (5.1 mmol) of 17-bromo-2,5,8,11-tetraoxaheptadecane, $Eg_3C_6Br$ (compound (2)) and 1.0 g (5.6 mmol) of potassium phthalimide were dissolved in 40 ml of N,N-dimethylformamide and then stirred at 90° C. for 2 hours. After this was restored to room temperature, the solvent was evaporated away, water was added to the residue followed by extraction with diethyl ether. This was dried with magnesium sulfate, and the solvent was evaporated away to give 2.04 g of a colorless transparent liquid of 2-(2,5,8,11-tetraoxaheptadecan-17-yl)isoindoline-1,3-dione (compound (3)).

IR (NaCl, cm$^{-1}$) 2930, 2858, 1772, 1714, 1615, 1467, 1438, 1396, 1368, 1301, 1248, 1188, 1109, 947, 878, 852, 795, 721

$^1$H NMR (CDCl$_3$, 270 MHz) δ 7.84 (dd, J=5.4 Hz, J=3.4 Hz, 2H), 7.71 (dd, J=5.4 Hz, J=3.4 Hz, 2H), 3.41-3.70 (m, 14H), 3.43 (t, J=6.7 Hz, 2H), 3.38 (s, 3H), 1.54-1.69 (m, 6H), 1.25-1.30 (m, 6H)

FABMS (m-nitrobenzyl alcohol) m/z 422.4 [M+1], 444.4 [M+Na]

<Production of Compound (4) According to Production Method 3>

1.9 g (4.5 mmol) of 2-(2,5,8,11-tetraoxaheptadecan-17-yl) isoindoline-1,3-dione (compound (3)) and 0.88 ml (18.0 mmol) of hydrazine monohydrate were dissolved in 50 ml of ethanol, and heated under reflux for 2 hours. After this was restored to room temperature, the solvent was evaporated away. The resulting white solid was dispersed in diethyl ether and filtered through Celite to give 1.30 g of a colorless transparent liquid of 17-amine-2,5,8,11-tetraoxaheptadecane (compound (4)).

IR (NaCl, cm$^{-1}$) 3366, 2926, 2856, 1646, 1596, 1458, 1351, 1300, 1248, 1200, 1110, 1030, 942, 851, 724

$^1$H NMR (CDCl$_3$, 270 MHz) δ 3.54-3.70 (m, 12H), 3.45 (t, J 6.7 Hz, 2H), 3.38 (s, 3H), 2.67 (t, J=6.7 Hz, 2H), 1.22-1.58 (m, 12H)

FABMS (m-nitrobenzyl alcohol) m/z 292.4 [M+1], 314.4 [M+Na]

<Production of Compounds (6) and (7)>

Compounds (6) and (7) were produced with reference to *J. Am. Chem. Soc.* 2002, 124, 14759-14769.

315 mg (1.2 mmol) of 1,3,5-benzenetricarbonyl trichloride (compound (5)) was dissolved in 2 ml of tetrahydrofuran, and stirred on an ice bath. A solution of 772 mg (11.9 mmol) of sodium azide dissolved in 3 ml of water was dropwise added thereto, taking 5 minutes, and then stirred for 2 hours on an ice bath. An aqueous saturated sodium hydrogencarbonate solution was added thereto followed by extraction with toluene, and the organic layer was washed with an aqueous saturated sodium hydrogencarbonate solution and saturated saline water. Subsequently, this was dried with magnesium sulfate and concentrated until the solution amount could reach 10 ml or so, thereby giving a toluene solution of 1,3,5-benzenetricarbonyl triazide (compound (6)). The formation of the compound (6) was confirmed by IR. The solution was stirred at 90° C. for 2 hours to give a toluene solution of 1,3,5-benzenetricarbonyl triisocyanate (compound (7)). The formation of the compound (7) was confirmed by IR.

<Production of Compound (8) According to Production Method 4>

The toluene solution of the compound (7) was stirred on an ice bath, to which dropwise added was a solution of 1.14 g (3.9 mmol) of the compound (4) dissolved in 3 ml of methylene chloride. With gradually heating up to room temperature, this was stirred overnight. After the solvent was evaporated away, the residue was reprecipitated with methylene chloride and diethyl ether and purified through silica gel column chromatography (chloroform/methanol/triethylamine) to give 451 mg of a white solid of 1,1',1''-(benzene-1,3,5-triyl)tris{3-(2,5,8,11-tetraoxaheptadecan-17-yl)urea} (compound (8)).

IR (KBr, cm$^{-1}$) 3394, 2927, 2857, 1679, 1619, 1544, 1456, 1351, 1239, 1105, 851

$^1$H NMR (DMSO-d$_6$, 270 MHz) δ 8.25 (s, 3H), 7.07 (s, 3H), 5.93 (t, J=6.0 Hz, 3H), 3.34-3.48 (m, 42H), 3.22 (s, 9H), 3.03 (q, J=6.0 Hz, 6H), 1.26-1.53 (m, 36H)

FABMS (m-nitrobenzyl alcohol) m/z 1075.9 [M+1], 1097.8 [M+Na]

Anal. Calcd for C$_{54}$H$_{102}$N$_6$O$_{15}$ 3.5H$_2$O: C, 58.21; H, 9.67; N, 8.23.

Found: C, 58.10; H, 9.63; N, 8.23.

<Confirmation of Formation of Hydrogel>

Two ml of deionized water was added to 1 mg of the compound (8), which was dissolved by ultrasonication with cooling in an ice bath. With gradually heating up to room temperature, this was statically left as such for 30 minutes. As shown in FIG. 1, this was a transparent solution at 0° C. (left of FIG. 1), but formed a hydrogel after heated up to room temperature (right of FIG. 1), and no solution dropped out of the bottle even when inverted.

<Confirmation of Temperature Responsiveness>

Figure 2:
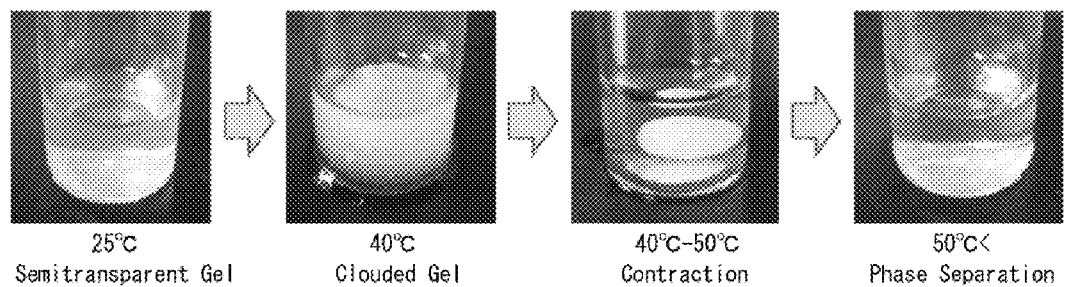
FIG. 2 includes photographic pictures showing the temperature responsiveness of a thermal responsive molecule (hydrogelling agent) of the invention.

This is for investigating the temperature responsiveness of 0.1 wt. % hydrogel. As shown in the photographs of FIG. 2, a semitransparent hydrogel was formed at room temperature (about 25° C.) and then heated up to 40° C., whereupon clouding of the hydrogel was observed. When this was further heated, contraction of the hydrogel was observed, and at about 50° C. or higher, complete phase separation occurred.

<IR Analysis>

Figure 3:
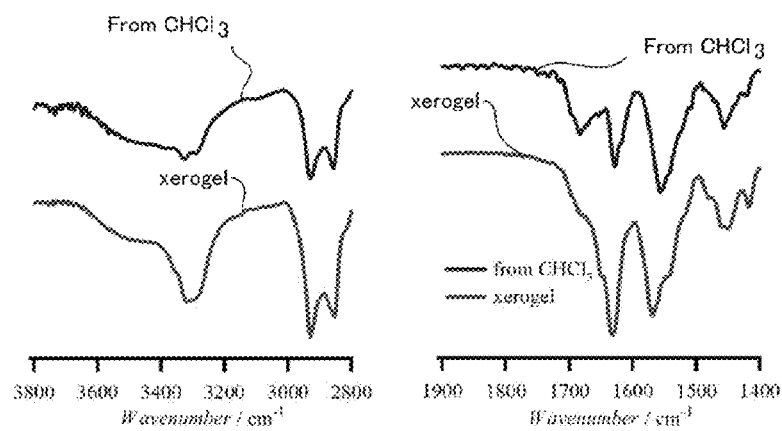
FIG. 3 includes IR spectra of a xerogel obtained from a thermal responsive molecule (hydrogelling agent) of the invention and a solid sample.

The xerogel formed by freeze-drying 0.1 wt. % hydrogel and a solid formed by drying a chloroform solution were IR-analyzed. The found data are shown in FIG. 3. As obviously in FIG. 3, the xerogel exhibited strong N—H stretching vibration at 3319 cm$^{-1}$, shift of amide I absorption band to the lower wavenumber side of from 1684 cm$^{-1}$ to 1632 cm$^{-1}$ and shift of amide II absorption band to the higher wavenumber side of from 1557 cm$^{-1}$ to 1569 cm$^{-1}$, as compared with the solid obtained from chloroform. These are all considered to be derived from the strong hydrogen bonding between ureal moieties, and it is considered that a strong hydrogen bonding network would be formed in the hydrogel.

<TEM Analysis>

One ml of deionized water was added to 1 mg of the compound (8), and a hydrogel was formed according to the same method as above. Five μl of the hydrogel of the compound (8) was put on an elastic carbon supporting film (grid pitch, 100 μm; by Okenshoji Co., Ltd.), and after one minute, the excessive solution was absorbed by filter paper, and this was kept dried overnight at room temperature. Subsequently, this was stained with 5 μl of an aqueous 2% uranium acetate solution; and after 1 minute, the excessive solution was absorbed by filter paper, and this was observed with a transmission electronic microscope (TEM, JEOL's JEM 2000 EX) to confirm the morphology thereof. The result is shown in FIG. 4.

Figure 4:
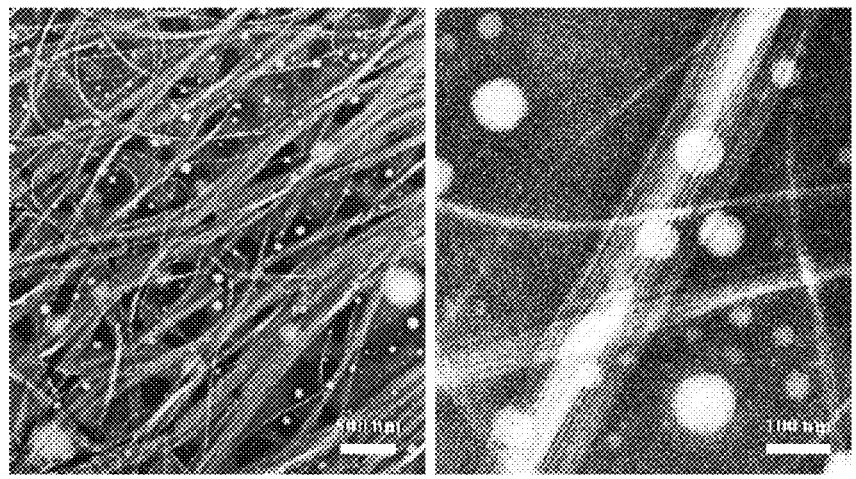
FIG. 4 includes transmission electromicroscopic (TEM) pictures of a thermal responsive molecule (hydrogelling agent) of the invention.

As in FIG. 4, the compound (8) forms a fiber-like structure having a thickness of around 10 nm or so in an aqueous solution, and it is considered that the fibers would form a three-dimensional network structure to give a hydrogel.

<SEM Analysis>

Figure 5:
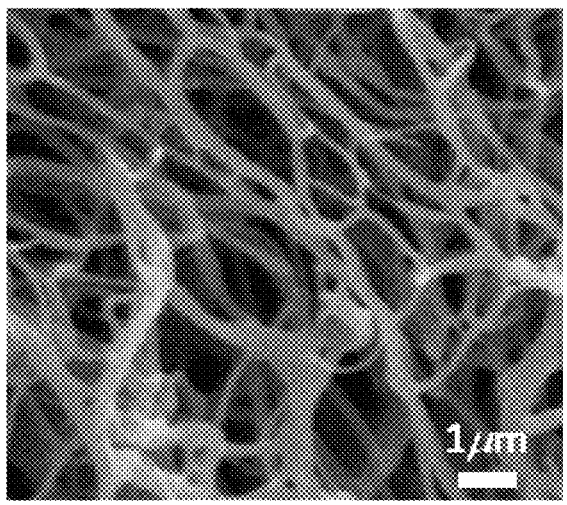
FIG. 5 is a scanning electromicroscopic (SEM) picture of a xerogel obtained from a thermal responsive molecule (hydrogelling agent) of the invention.

A carbon seal was stuck to a SEM sample stand, and the xerogel of the compound (8) was sprayed over it. Subsequently, this was ion-coated with Au, and analyzed through SEM to confirm the morphology thereof. The result is shown in FIG. 5. As obvious from FIG. 5, the fibers formed a three-dimensional network structure, like in TEM analysis.

<Fluorescent Spectrum>

Figure 6:
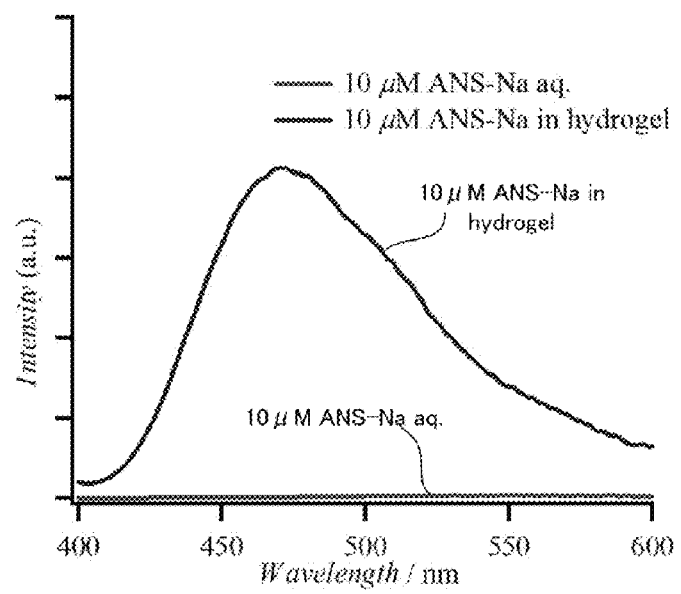
FIG. 6 is a graph of a fluorescent spectrum showing incorporation of a fluorescent substance in a thermal responsive molecule (hydrogelling agent) of the invention.

Using ANS-Na (8-anilino-1-naphthalene sulfonic acid sodium salt) known as a hydrophobic environmental probe, the hydrogel was tested for incorporation of a fluorescent substance thereinto. FIG. 6 shows a fluorescent spectrum of 10 μM ANS-Na aqueous solution and that of 10 μM ANS-Na hydrogel (1 mM Eg$_3$C$_8$U aqueous solution).

As obvious from FIG. 6, it is confirmed that ANS-Na showed extremely weak fluorescence in the aqueous solution, but its fluorescent intensity increased in the hydrogel and was shifted to the short wavelength side. The reason for this is considered that ANS-Na could be incorporated in the fiber structure of $Eg_3C_8U$ and would exist in the hydrophobic environment.

Figure 7:
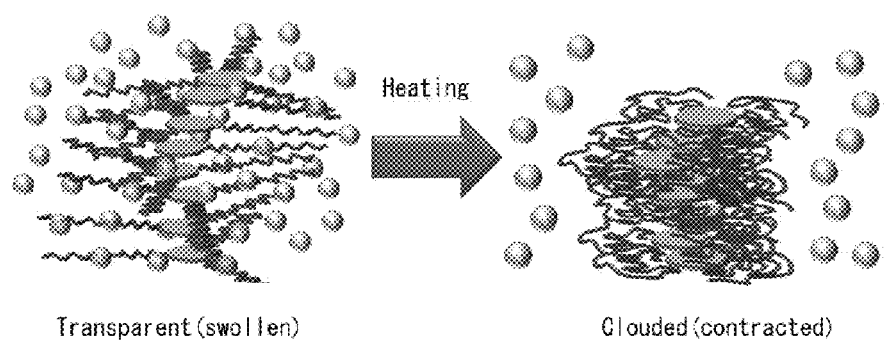
FIG. 7 includes images showing a hydrated state (left) of the column structure of a thermal responsive molecule (hydrogelling agent) of the invention, and a dehydrated state (right) thereof.

As described in the above, there was obtained a thermal responsive low-molecular hydrogelling agent that gelled when heated in an extremely diluted, 0.05 wt. % aqueous solution. IR analysis of the hydrogel confirmed the presence of strong hydrogen-bonding network between ureal moieties; and morphology analysis with SEM and TEM revealed the formation of the gel structure through three-dimensional network entangling of fiber-like aggregates. Further, it has been confirmed the hydrogel could get clouded to cause phase separation when heated up to 40° C. or higher. The reason for the series of characteristic temperature behavior is considered that the hydrated structure of the triethylene glycol chain formed at a low temperature could be rapidly dehydrated owing to the attenuation of the hydrogen bonding to water molecules along with the temperature increase. The condition is shown in FIG. 7 as a schematic drawing thereof.

An incorporation experiment of ANS-Na, which is the hydrophobic environmental probe, confirmed the presence of a hydrophobic condition in the hydrogel, in which the incorporation of hydrophobic molecules from hydrophilic molecules in some degree could be expected. The low-molecules hydrogelling agent having such a highly-biocompatible PEG chain in the surface thereof is considered to have excellent biocompatibility, and its development to DDS such as slow-release preparations is expected, for example, for application to wound-covering materials to cure wounds such as surface wounds or burn wounds in a wet environment and by enveloping chemicals in the hydrogelling agent.

Figure 8:
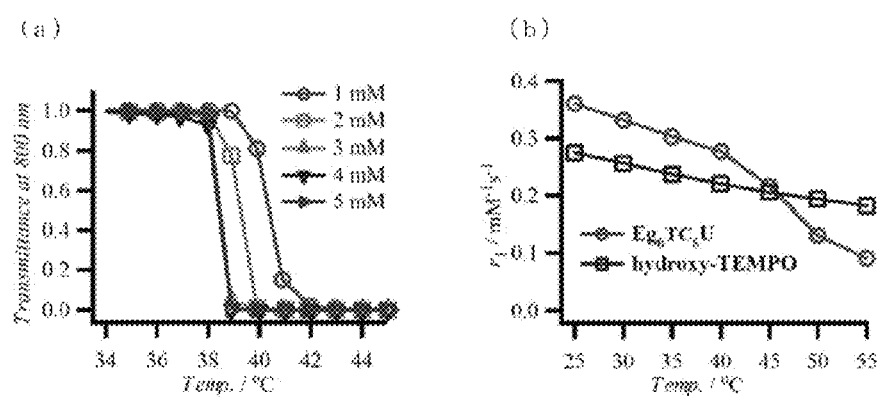
FIG. 8 includes graphs each showing the characteristics of a thermal responsive molecule ($Eg_6TC_6U$) of the invention; in which (a) is a graph showing cloudiness at LCST or higher, and (b) is a graph showing relaxivity reduction at LCST or higher.

Next, a TEMPO radical-having derivative, $Eg_6TC_6U$ was produced. Regarding its production method, $Eg_6TC_6U$ was produced from (4-((2-(6-bromohexylloxy)ethyl)(2-(2-(2-methoxyethoxy)ethoxyl)ethyl)amino-9-1-oxy-2,2,6-tetramethylpiperidine) ($Eg_3TC_6Br$) in the same manner as that for the above-mentioned $Eg_3C_8U$ production method. The transmittance of the $Eg_6TC_6U_{aq}$ and the temperature-dependent relaxivity change per radical of $Eg_6TC_6U$ were measured. The found data are shown in FIG. 8. As in FIG. 8, $Eg_6TC_6U$ having the organic radical has LCST at around 40° C. or so, and showed cloudy solution at higher than LCST (left of FIG. 8). In water-proton vertical relaxation time measurement in pulse NMR, significant relaxivity reduction was detected over the LCST (right of FIG. 8). This result indicate the reduction of the contact between the radical and the water molecule as formation of the aggregate.

$Eg_6TC_6U$ having the TEMPO radical showed LCST when heated in an aqueous solution, and its aggregation behavior was confirmed, but it did not exhibit the behavior of hydrogel. This is because the resulting aggregate does not form a three-dimensional network like in $Eg_3C_8U$.

INDUSTRIAL APPLICATION FIELDS

The thermal responsive molecule having a highly-biocompatible PEG chain in the surface thereof (low-molecular hydrogelling agent, etc.) of the invention has excellent biocompatibility, and its development to DDS such as slow-release preparations is expected, for example, for application to wound-covering materials to cure wounds such as surface wounds or burn wounds in a wet environment and by enveloping chemicals in the molecule.

What is claimed is:

1. A thermal responsive molecule of general formula (1), in which an amphiphilic side chain obtained by bonding a hydrophilic side chain and a hydrophobic group is introduced into a $C_3$-symmetric disc-shaped molecular skeleton:

$$Eg_nC_mU \qquad (1)$$

wherein Eg represents ethylene glycol; n indicates an integer of from 3 to 10; C represents an aliphatic hydrocarbon group; m indicates an integer of from 2 to 15; and U represents an urea skeleton.

2. The thermal responsive molecule according to claim 1, wherein U is 1,3,5-benzenetriyltriurea or 1,3,5-benzenetriyltriamide.

3. The thermal responsive molecule according to claim 1, wherein n is 3, m is 8, and U is 1,3,5-benzenetriyltriurea.

4. The thermal responsive molecule according to claim 3, wherein the thermal responsive molecule is a low-molecular hydrogelling agent.

* * * * *